United States Patent [19]

Weng et al.

[11] Patent Number: 4,629,690

[45] Date of Patent: * Dec. 16, 1986

[54] HOMOGENEOUS ENZYME SPECIFIC BINDING ASSAY ON NON-POROUS SURFACE

[75] Inventors: Litai Weng, Mountain View; Ian Gibbons, Palo Alto; Edwin F. Ullman, Atherton, all of Calif.

[73] Assignee: Syntex (U.S.A.) Inc., Palo Alto, Calif.

[*] Notice: The portion of the term of this patent subsequent to Jun. 23, 1998 has been disclaimed.

[21] Appl. No.: 561,987

[22] Filed: Dec. 14, 1983

Related U.S. Application Data

[63] Continuation of Ser. No. 303,326, Sep. 18, 1981, abandoned.

[51] Int. Cl.$^4$ ............................................ G01N 33/543
[52] U.S. Cl. ............................................ 435/7; 435/18; 435/25; 435/27; 435/28; 435/175; 435/810; 436/501; 436/518
[58] Field of Search .................. 435/4, 7, 188, 805, 435/810, 28, 175; 424/7.1; 422/55, 56, 57, 61, 69; 436/518

[56] References Cited

U.S. PATENT DOCUMENTS

| | | | |
|---|---|---|---|
| Re. 29,169 | 4/1977 | Schuurs et al. | 435/7 |
| 3,654,090 | 4/1972 | Schuurs et al. | 435/7 |
| 4,233,402 | 11/1980 | Maggio et al. | 435/7 |
| 4,275,149 | 6/1981 | Litman et al. | 435/7 |
| 4,299,916 | 11/1981 | Litman et al. | 435/7 |
| 4,391,904 | 7/1983 | Litman et al. | 435/188 |

*Primary Examiner*—Sidney Marantz
*Assistant Examiner*—David A. Saunders
*Attorney, Agent, or Firm*—Theodore J. Leitereg; Bertram I. Rowland

[57] ABSTRACT

Enzyme channeling assay is provided employing a solid non-porous surface to which is bound a member of a specific binding pair and an enzyme. A complementary member of a specific binding pair is conjugated to second enzyme, so that the amount of second enzyme which becomes bound to said solid non-porous surface by the binding of a specific binding pair(s) is related to the amount of analyte in the liquid assay medium with which the solid surface is in contact. The first and second enzymes are related by the product of one being the substrate of the other. The turnover of the substrate formed by one of the enzymes results in a detectable product, which can be related to the amount of analyte in the medium.

16 Claims, No Drawings

HOMOGENEOUS ENZYME SPECIFIC BINDING ASSAY ON NON-POROUS SURFACE

This is a continuation of application Ser. No. 303,326, filed Sept. 9, 1981, now abandoned.

BACKGROUND OF THE INVENTION

1. Field of the Invention

There are continuous efforts to develop new flexible techniques for the determination of a wide variety of analytes. The methods are related to new situations, new equipment, simplified protocols, greater sensitivity and the like. In many instances it is desirable to be able to carry out competitive protein binding assays in microtiter plates. It is also desirable not to have to perform wash steps, but rather to be able to combine all the reagents and sample in the well and after sufficient time, be able to read a signal.

2. Description of the Prior Art

Immunoassays employing porous particles and two enzymes are described in application Ser. No. 964,099, now U.S. Pat. No. 4,275,149. See also U.S. Pat. No. 4,233,402, for a description of channeling immunoassays in a homogeneous medium.

SUMMARY OF THE INVENTION

Competitive protein binding assays are provided where a member of a specific binding pair and a first enzyme are bound to a solid non-porous surface, particularly the wall of a container e.g. microtiter plate. A reagent is provided combining a second enzyme conjugated to a complementary member of a specific binding pair, where the amount of the enzyme conjugate which binds to the solid surface is related to the amount of analyte in the aqueous assay medium. The enzymes are related by the product of one being the substrate of the other. The amount of a detectable product which is formed as a result of turnover by one of the enzymes of a substrate produced by the other enzyme is related to the amount of analyte in the medium.

DESCRIPTION OF THE SPECIFIC EMBODIMENTS

A competitive protein binding assay is provided which employs a solid non-porous surface for binding a member of a specific binding pair and an enzyme. The solid surface is in contact with an aqueous assay medium which contains the analyte from a sample and a reagent which is a conjugate of an enzyme and a member of a specific binding pair which binds to the surface in proportion to the amount of analyte in the medium. Also included are any necessary substrates or reactants for production of a product which provides a detectable signal.

The various assay participants in the liquid medium may be added in a variety of sequences to provide different protocols, depending upon the nature of the analyte and the reagents. The two enzymes and ancillary materials are components of a signal producing system which results in a detectable product. By relating the amount of detectable product which is produced with an unknown sample, as compared to the amount of the detectable product produced with known amounts of analyte, the concentration of analyte in the sample can be determined quantitatively.

The analyte will be a member of a specific binding pair consisting of the ligand and its homologous receptor. One of the members of the specific binding pair will be stably bound, either directly or indirectly, either covalently or non-covalently, to the solid non-porous surface. There is an exception where a specific type of receptor to a specific ligand is the analyte, three specific binding components are required, viz. receptor, antireceptor or ligand, which may be bound to the solid surface, and ligand or anti-receptor respectively, employed for the enzyme labeling. Thus, receptor as an analyte allows for a number of alternative conjugates. In addition, one of the enzymes of the signal producing system will be bound or become bound to the reciprocal member of the specific binding pair. By appropriate choice of specific binding pair conjugates, the amount of the enzyme conjugate bound to the solid surface can be related to the amount of analyte in the assay medium.

In carrying out the method, one starts with the solid surface, normally the container wall, having been preprepared by binding to the surface a member of the specific binding pair and a first enzyme. Various protocols are employed, depending upon the nature of the analyte and the nature of the components of the signal producing system. In the most general sense, the sample and reagents are combined in a buffered aqueous medium to insure that the amount of the enzyme conjugate which binds to the surface is related to the amount of analyte in the sample. A component of the signal producing system results in production of a product which provides a detectable signal in an amount relative to the turnover of the enzyme which employs as its substrate the product of the other enzyme. By determining the amount of signal, one can relate the signal to the amount of analyte in the medium.

DEFINITIONS

Analyte—the compound or composition to be measured, which may be a ligand, which is mono- or polyepitopic, antigenic or haptenic, a single or plurality of compounds which share at least one common epitopic or binding site or a receptor.

Specific binding pair—two different molecules, where one of the molecules has an area on the surface or in a cavity which specifically binds to a particular spatial and polar organization of the other molecule. The members of the specific binding pair are referred to as ligand and receptor (antiligand). For the most part, specific binding pairs will relate to haptens and antigens as ligand and antibodies as receptors. To that extent, these groups will be considered as members of an immunological pair. Since the acronym is "mip," the term mip will be used in the generic sense to include specific binding pairs, whether immunological pairs or not.

Ligand—any organic compound for which a receptor naturally exists or can be prepared.

Receptor (antiligand)—any compound or composition capable of recognizing a particular spatial and polar organization of a molecule e.g. epitopic site. Illustrative receptors include naturally occurring receptors, e.g. thyroxine binding globulin, antibodies, enzymes, Fab fragments, lectins and the like.

Ligand Analog—a modified ligand which can compete with the analogous ligand for a receptor, the modification providing means to join a ligand analog to another molecule. The ligand analog will normally differ from the ligand by more than replacement of a hydrogen with a bond which links the ligand analog to a hub or label.

Poly(ligand-analog)—a plurality of ligands or ligand analogs joined together covalently, normally to a hub nucleus. The hub nucleus is a polyfunctional material, normally polymeric, usually having a plurality of functional groups e.g. hydroxy, amino, mercapto, ethylenic, etc. as sites for linking. The hub nucleus may be water soluble or insoluble, preferably water soluble, and will normally be at least about 35,000 molecular weight and may be 10 million or more molecular weight, but usually under 600,000, more usually under 300,000. Illustrative hub nucleii include polysaccharides, polypeptides, including proteins, nucleic acids, ion exchange resins and the like. Water insoluble hub nucleii can be the same as those indicated for the particle.

Solid surface—the solid surface may be any non-porous solid surface which allows for binding, either covalent or non-covalent, of the mip and the enzyme to its surface. The binding may be direct or indirect, for example, through the intermediacy of a specific binding pair. The solid surface may be coated or uncoated to aid the binding of the necessary components of the assay to the surface or to inhibit the non-specific binding of components to the surface. While for the most part, the solid surface will be the container wall or vanes in the vessel, solid non-porous particles may also be employed by themselves or in combination with the container walls. The particles will be of a size in the range of about 100 nm to about 1 mm, usually not more than about 10$\mu$.

Signal producing system—the signal producing system has as its basis two enzymes which are related by the product of one being the substrate of the other. Therefore, when the two enzymes are in close propinquity a greater turnover would be expected of the product of the first enzyme in the series by the second enzyme in the series. Therefore, there will be at least one compound as part of a signal producing system which is capable of being modified by a first enzyme to produce a product which will be modified by a second enzyme to produce a second product which, directly or indirectly provides a detectable signal. However, many other components may be included in the signal producing system which may be necessary for the enzymatically catalyzed reaction or to interact or react with the product of the second enzyme to provide a detectable signal. For the most part, the signal will be the absorption or emission of electromagnetic radiation, usually in the ultraviolet or visible range, but electrochemical changes, thermal changes, nephelometric changes, and the like may also find application.

Mip-enzyme-conjugate—a conjugate either ligand or receptor conjugated with one of the two enzymes which are components of the signal producing system. The mip may or may not be the analyte or its complementary pair member. As appropriate, the conjugate may be referred to as the ligand-enzyme conjugate or the receptor-enzyme-conjugate.

METHOD

The subject assay is carried out in an aqueous zone at a moderate pH, generally close to optimum assay sensitivity, without separation of the assay components or products. The assay zone for the determination of analyte is prepared by employing an appropriate aqueous medium, normally buffered, the unknown sample, which may have been subject to prior treatment, the solid surface to which is bound a mip and an enzyme, the mip-enzyme-conjugate, all of the remaining materials required for the signal producing system for producing a detectable signal, as well as mips or mip analogs, as required.

The presence of analyte in the unknown will affect the partition of the mip-enzyme-conjugate between the solid surface and the bulk solution in the assay medium.

In carrying out the assay, an aqueous medium will normally be employed. Other polar solvents may also be included, usually oxygenated organic solvents of from 1–6, more usually from 1–4 carbon atoms, including alcohols, ethers and the like. Usually these cosolvents will be present in less than about 40 weight percent, more usually in less than about 20 weight percent.

The pH for the medium will usually be in the range of about 4–11, more usually in the range of about 5–10, and preferably in the range of about 6.5–9.5. The pH is chosen so as to maintain a significant level of specific binding by the receptor while optimizing signal producing efficiency. In some instances, a compromise will be made between these two considerations. Various buffers may be used to achieve the desired pH and maintain the pH during the determination. Illustrative buffers include borate, phosphate, carbonate, Tris, barbital and the like. The particular buffer employed is not critical to this invention, but in individual assays, one buffer may be preferred over another.

Moderate temperatures are normally employed for carrying out the assay and usually constant temperatures during the period of the measurement, particularly for rate determinations. The temperatures for the determination will generally range from about 10°–50° C., more usually from about 15°–40° C.

The concentration of analyte which may be assayed will generally vary from about $10^{-4}$ to $10^{-15}$M, more usually from about $10^{-6}$ to $10^{-13}$M. Considerations such as whether the assay is qualitative, semi-quantitative or quantitative, the particular detection technique and the concentration of the analyte of interest will normally determine the concentration of the other reagents.

While the concentrations of the various reagents in the assay medium will generally be determined by the concentration range of interest of the analyte, the final concentration of each of the reagents will normally be determined empirically to optimize the sensitivity of the assay over the range of interest. The total binding sites of the members of the specific binding pair which are reciprocal to the analyte will be not less than about 0.1 times the minimum concentration of interest based on analyte binding sites, usually about 0.1 to 100 times, more usually about 0.3–10 times the maximum concentration of interest. By concentration is intended the available concentration, that is, the concentration at saturation, and not necessarily the actual concentration where members of the specific binding pair may not be equally available for binding.

Depending upon the nature of the reagents, as well as the protocol, the concentrations of individual reagents can be varied widely. For example, if the analyte is an antigen, and the mip bound to the solid surface and the mip and the mip-enzyme-conjugate are both receptors for the antigen, one could have very large excesses of the mip on the surface as compared to the total amount of antigen. One would normally not have large excesses of the mip-enzyme-conjugate, except when the product of the enzyme bound to the solid surface is extremely short lived or a scavenger is provided in the bulk solution to maintain the concentration of the product in the bulk solution at an extremely low level.

The order of addition of the components may be varied depending upon whether an equilibrium mode or rate mode is employed, as well as the nature of the mips employed.

Since with many receptors, the association of the mips is almost irreversible during the time period of the assay, one will normally avoid adding the mip-enzyme-conjugate to the solid surface before the sample, where the mip reciprocal to the mip of the conjugate is bound to the surface. This would not be a concern, where the analyte is polyvalent and both the mip on the surface and the mip of the mip-enzyme-conjugate are the same. This is also true where monoclonal antibodies are employed which are directed to different sites on the analyte. Regardless of the nature of the analyte, all the components can be added simultaneously and either a rate or equilibrium determination made.

While it is usually desirable to avoid washing steps, in some situations it will be preferable to add the sample to the solid surface incubate and wash to remove endogenous materials which might interfere with the signal producing system.

One or more incubation steps may be involved in the assay. For example, it may be desirable to incubate an antigen analyte with the surface or, alternatively, with the mip-enzyme-conjugate prior to combining the other components. In some instances it may be desirable to combine the analyte and the other mip-containing components prior to adding some or all of the substrate components. Whether to employ an incubation period and the length of the incubation period will depend to a substantial degree on the mode of determinaton -rate or equilibrium- and the rate of binding of the complementary mip. Usually, incubation steps will vary from about 0.5 min. to 24 hours, more usually from about 5 min. to 1 hour. Incubation temperatures will generally range from about 4°–50° C., more usually from about 15°–37° C.

After the reagents are combined, the signal will then be determined. One or more readings may be involved, frequently the difference in signal level over a predetermined time interval will be employed. The method of determination may be the observation of electromagnetic radiation, particularly ultraviolet and visible light, either absorption or emission, colorimetric, electrochemical, nephelometric, or the like. Desirably, the signal will be read as electromagnetic radiation in the ultraviolet or visible region, particularly from about 250 to 750 nm, usually from about 350 to 650 nm.

The temperature at which the signal is observed will generally range from about 10° to 50° C., more usually from about 15° to 40° C.

Standard assay media can be prepared which have known amounts of the analyte. The observed signal for the standard assay media may then be plotted, so as to relate concentration to signal. Once a standard curve has been established, a signal may be directly related to the concentration of the analyte.

The time for measuring the signal will vary depending on whether a rate or equilibrium mode is used, the sensitivity required, the nature of the signal producing system and the like. For a rate mode, the times between readings will generally vary from about 5 sec to 6 hrs, usually about 10 sec to 1 hr. For the equilibrium mode, after a steady state is achieved, a single reading may be sufficient or two readings over any convenient time interval may suffice.

The ligand may be mono- or polyepitopic. By epitopic is intended a specific site on a molecule to which another molecule will specifically bind. In a number of situations, whether the ligand is mono- or polyepitopic will not affect the manner in which the assay is performed. Where the analyte is a ligand, the mip bound to the surface may be either ligand or receptor, usually receptor. The mip-enzyme-conjugate can have either ligand or receptor. However, where both the mip bound to the surface and the mip-enzyme-conjugate are receptor, the ligand must be polyepitopic or made so by employing a poly(ligand analog) as an additional reagent. That is, a sandwich technique is employed where the ligand binds to the mip bound to the surface and provides ligand epitopic sites for binding of the mip-enzyme-conjugate to the surface.

Where the receptor is the analyte, the mip bound to the surface and the mip-enzyme-conjugate may have the same or different mips, with the proviso that receptor is polyvalent when ligand is involved in both conjugates.

In the event that the analyte, the mip bound to the surface and the mip-enzyme-conjugate all are or contain the same type of mip, unless monoclonal antibodies are involved, then the homologous member must be added and must be provided in polyepitopic form, either as an antibody or other polyvalent receptor, where it is a receptor, or as a polyhapten(poly(ligand analog)), where it is a ligand.

It should be appreciated that the mip-enzyme-conjugate need not be complementary to the analyte. In many instances it may be desirable that the mip-enzyme-conjugate recognize the receptor, so that a plurality of enzymes will bind to the receptor which is complementary to the ligand.

MATERIALS

The components employed in the assay will be the sample containing the analyte, the solid surface to which the mip and the enzyme of the signal producing system are bound, the mip-enzyme-conjugate, the remaining members of the signal producing system, and, as appropriate, mips. Employed in the preparation of the agents will be the solid surface and enzymes.

Analyte

The ligand analytes of this invention are characterized by being monoepitopic or polyepitopic. The polyepitopic ligand analytes will normally be poly(amino acids) e.g. polypeptides and proteins, polysaccharides, nucleic acids, and combinations thereof. Such combinations or assemblages include bacteria, viruses, chromosomes, genes, mitochondria, nuclei, cell membranes, and the like.

For the most part, the polyepitopic ligand analytes employed in the subject invention will have a molecular weight of at least about 5,000, more usually at least 10,000. In the poly(amino acid) category, the poly(amino acids) of interest will generally be from about 5,000 to 5,000,000 molecular weight, more usually from about 20,000 to 1,000,000 molecular weight; among the hormones of interest, the molecular weights will usually range from about 5,000 to 60,000 molecular weight.

A wide variety of ligands are described in U.S. Pat. No. 4,193,983, which description is incorporated herein by reference. Also, a description of ligand analog may be found in this reference, which description is also incorporated herein by reference.

Signal Producing System

The signal producing system will have at least three components: The first and second enzymes, where the enzymes are related by the product of the first enzyme being the substrate of the second enzyme, and the substrates of both enzymes. Additional components may be necessary for one or both of the enzyme catalyzed reactions or for interacting or reacting with the product of the second enzyme to provide a detectable signal.

The signal producing systems will provide, for the most part, a product which provides for a measurement of electromagnetic radiation, such as a chromophore which absorbs light, or provides light emission, such as fluorescers or chemiluminescers.

In choosing an enzyme, in addition to the effect of the particle on the enzyme turnover rate, other considerations will also affect the choice of enzyme. These considerations include the stability of the enzyme, the desirability of a high turnover rate, the sensitivity of the rate to variations in the physical environment, the nature of the substrate or product, preferably the product, the availability of the enzyme, the effect of conjugation of the enzyme on the enzyme's properties, the effect on enzyme activity of materials which may be encountered in the sample solutions, the molecular weight of the enzyme, and the like.

In the aforesaid patent references, there is an extended description of enzymes, which description is incorporated herein by reference.

Various combinations of enzymes may be employed. In one set of combinations, the ability to measure NAD and NADP or their reduced products is employed. In these combinations, oxidoreductases dependent on NAD are employed with an enzyme which provides a substrate for the oxidoreductases. A wide variety of enzyme types and reactions may be employed to produce the measured product, many of the enzymes being part of carbohydrate metabolism. A substantial number of these enzymes will be involved in the formation and transformation of phosphate esters. Among other reactions which may be involved are carbon-carbon bond cleavage by lyases, isomerization involving keto-aldehyde transformations, and decarboxylation.

Of particular interest are combinations involving sugars, where in a first step a transferase, hydrolase, lyase or isomerase, particularly involving a phosphate ester, produces a substrate of NAD(P) dependent oxidoreductase. Particularly useful are mono-phosphate mono-saccharides of from 3 to 6 carbon atoms as enzyme substrates in the oxidoreductase reaction.

The following table indicates a number of illustrative examples where precursors for oxidoreductases are formed and the course of the reaction of the NAD dependent enzymes is followed by the transformation of the NAD or NADP to or from its reduced form. In each example both enzymes are part of the signal producing system.

TABLE I

| Category I.U.B | | Enzyme | Exemplary Reaction |
|---|---|---|---|
| 1. | 2.7.1 | Hexokinase | glucose + ATP → glucose-6-phosphate + ADP |

TABLE I-continued

| Category I.U.B | | Enzyme | Exemplary Reaction |
|---|---|---|---|
| | 1.1.1 | glucose-6-phosphate dehydrogenase | glucose-6-phosphate + NADP → 6-P—glucuronate + NADPH |
| 2. | 4.1.2 | aldolase | fructose-1,6-diP → dihydroxyacetone-P + glyceraldehyde-3-P |
| | 1.2.1 | glyceraldehyde-P dehydrogenase | glyceraldehyde-3-P + NAD → 3-phosphoglycerate + NADH |
| 3. | 3.1.3 | alkaline phosphatase | dihydroxyacetone diphosphate → dihydroxyacetone phosphate |
| | 1.2.1 | glycerol-3-P dehydrogenase | dihydroxyacetone phosphate + NADH → glyceryl phosphate + NAD |
| 4. | 2.7.1 | pyruvate kinase | phosphoenol pyruvate + ADP → pyruvate + ATP |
| | 1.1.1 | lactate dehyrognase | pyruvate + NADH → lactate + NAD |
| 5. | 3.1.3 | alkaline phosphatase | 1,6-glucosyl diphosphate → G-6-P |
| | 1.1.1 | glucose-6-phosphate dehydrogenase | G-6-P + NADP → 6-P-glucuronate + NADPH |
| 6. | 5.4.2 | triose phosphate isomerase | glyceraldehyde-3-P → dihydroxyacetone phosphate |
| | 1.2.1 | α-glycerol-3-P dehydrogenase | dihydroxyacetone phosphate + NADH → glyceryl phosphate + NAD |
| 7. | 3.1 3 | alkaline phosphatase | D-sorbitol phosphate → D-sorbitol |
| | 1.1.1 | α-D-hexitol dehydrogenase | D-sorbitol + NADP → α-D-glucopyranose + NADPH |
| 8. | 5.4.2 | phosphogluco mutase | α-glucose-1-phosphate → glucose-6-phosphate |
| | 1.1.1 | glucose-6-phosphate dehydrogenase | glucose-6-phosphate + NAD → 6-P-glucuronate + NADH |
| 9. | 4.1.1 | pyruvate decarboxylase | pyruvate → acetaldehyde |
| | 1.1.1 | alcohol dehydrogenase | acetaldehyde + NADH → ethanol + NAD |
| 10. | 4.2.1 | fumarase | fumarate → malate |
| | 1.1.1 | malate dehydrogenase | malate + NAD → oxalacetate + NADH |
| 11. | 4.2.1 | aconitase | cis-aconitate → isocitrate |
| | 1.1.1 | isocitrate dehydrogenase | isocitrate + NAD → α-oxoglutarate + NADH |

Another combination of enzymes involves the formation of hydrogen peroxide, where the resulting catalyzed reaction by peroxidase of the hydrogen peroxide with a chemiluminescent material, e.g. luminol, produces light. Besides luminol, other 2,3-dihydro-1,4-pthalazinediones may be employed. These include the 5-amino-6,7,8-trimethoxy- and dimethylamino[ca]benz analog. Other compounds are the 2,4,5-triphenylimidazoles, with lophine, as the common name for the parent, and the para-dimethylamino and—methoxy substituted compounds also finding use. The chemiluminescent compound may be the direct source of light or may be allowed to interact with an acceptor, such as 9,10-dibromoanthracene, which will then emit light. Alternatively one can provide a wide variety of dye precursors which will undergo enzymatically catalyzed reactions with hydrogen peroxide to produce the colored form which can be detected.

The following table indicates a number of these reactions in which both enzymes are components of the signal producing system.

TABLE II

| Enzyme Category | Enzyme | Exemplary Reaction |
|---|---|---|
| 1. 1.1.3 | glucose oxidase | glucose + $O_2$ → glucuronate + $H_2O_2$ |
| 1.11.1 | peroxidase | $H_2O_2$ + luminol → products + hu |
| 2. 1.7.3 | uricase | urate + $O_2$ → allantoin + $H_2O_2$ |
| 1.11.1 | peroxidase | $H_2O_2$ + O-dianisidine → dye |
| 3. 1.4.3 | D-amino acid oxidase | D-alanine + $O_2$ → pyruvate + $H_2O_2$ |
| 1.11.1 | catalase | $H_2O_2$ + Fe(CN)$_6$-4 → Fe(CN)$_6$-3 |
| 4. 1.2.3 | xanthine oxidase | xanthine + $O_2$ → uric acid + $H_2O_2$ |
| 1.11.1 | cytochrome C oxidase | $H_2O_2$ + pyrogallol → hydroxyquinone |

The next series of reactions are those which are based on two reactions involving water, normally the two reactions involving hydrolases, although synthetases may also be employed.

TABLE III

| Enzyme Category | Enzyme | Exemplary Reaction |
|---|---|---|
| 1. 3.1.3 | alkaline phosphatase | 1-umbelliferyl-$\beta$-galactoside-6-P → 1-umbelliferyl-$\beta$-galactoside |
| 3.2.1 | $\beta$-galactosidase | 1-umbelliferyl-$\beta$-galactoside → umbelliferone |
| 2. 3.1.1 | acetylesterase | 1-alizarinyl-$\beta$-glucoside-monoacetate → 1-alizarinyl-$\beta$-glucoside |
| 3.2.1 | $\beta$-glucosidase | 1-alizarinyl-$\beta$-glucoside → alizarin + glucose |
| 3. 3.2.1 | glucoamylase | 1-(p-nitrophenyl) 4-O—$\alpha$-D-glucopyranosyl $\beta$-D-glucose → 1-(p-nitrophenyl)$\beta$-D-glucoside |
| 3.2.1 | $\beta$-glucosidase | 1-(p-nitrophenyl) $\beta$-D-glucoside → 1-(p-nitrophenoxide + glucose |
| 4. 3.1.1 | cholinesterase | phenolphthalein $\beta$-glucuronide choline chloride ester → phenolphthalein $\beta$-glucuronide |
| 3.2.1 | $\beta$-glucuronidase | phenolphthalein $\beta$-glucuronide → $\beta$-glucuronide + phenolphthalein |
| 5. 3.4.1 | proline iminopeptidase | L-prolyl-L-leucine p-nitroanilide → L-leucine p-nitroanilide |
| 3.4.1 | aminopeptidase | L-leucine p-nitroanilide → L-leucine + p-nitroaniline |
| 6. 3.5.1 | urease | urea + $H_2O$ → $CO_2$ + $NH_3$ |
| 6.3.5 | NAD synthetase | ATP + deamidoNAD + $H_2O$ → ADP + $NH_3$ + NAD + pyrophosphate |
| 7. 3.1.3 | alkaline phosphatase peroxidase | 2,6 dichlorophenolindophenol-P → 2,6-dichlorophonolindophenol 2,6-dichlorophenolindophenol + $H_2O_2$ → dye |

The next series of combinations involves the preparation of a substrate in a first step for an enzyme which can donate or receive electrons from an acceptor or donor, with the result that there is a substantial change in the absorption spectrum of the acceptor or donor. For the most part, the second enzyme will be an oxidoreductase, particularly dehydrogenases and oxidases. In this series, both enzymes are components of the signal producing system.

TABLE IV

| Enzyme Category | Enzyme | Exemplary Reaction |
|---|---|---|
| 1. 3.1.1 | cholinesterase | butryl choline chloride → choline |
| 1.1.99 | choline dehydrogenase | choline + phenazine methosulfate → betaine aldehyde + dye (H) |
| 2. 2.7.1 | glycerol kinase | ATP + glycerol → L-glycerol-3-P |
| 1.1.99 | glycerol-phosphate dehydrogenase | L-glycerol-3-P + methylene blue → dihydroxyacetone phosphate + dye (H) |
| 3. 1.1.1 | glucose dehydrogenase | $\beta$-D-glucose + NADP → D-glucono-$\delta$-lactone + NADPH |
| 1.1.99 | gluconate dehydrogenase | D-gluconate + resazurin → 2-keto-D-gluconate + dye (H) |
| 4. 1.1.1 | alcohol dehydrogenase | ethanol + NAD → acetaldehyde + NADH |
| 1.6.2 | cytochrome $b_5$ reductase | NADH + indigotetrasulfonate → NAD + indigotetra sulfonate (H) |
| 5. 4.1.2 | deoxyribo-aldolase | 2-deoxy-D-ribose-5-phosphate → D-glyceraldehyde-3-P + acetaldehyde |
| 1.2.3 | aldehyde oxidase | acetaldehyde + 2,6-dichlorophenol-indophenol → acetic acid + dye (H) |
| 6. 1.1.1 | alcohol dehydrogenase | ethanol + NADP → acetaldehyde + NADPH |
| 1.6.99 | reduced NADP dehydrogenase | NADPH + trichlorophenolindophenol → NADP + trichlorophenolindophenol (reduced) |

In the subject invention, therefore, combinations are employed where a first enzymatic reaction is involved to provide a substrate for a second enzymatic reaction. The second enzymatic reaction results in directly or through additional reactions, the production of a compound which can be determined spectrophotometrically due to absorption of light, particularly over 300 nm, preferably over 350 nm, and more preferably over 400 nm; fluorescence, where the light emitted is of a wavelength greater than 350 nm, preferably greater than 400 nm, and more preferably greater than 450 nm; or through chemiluminescence. For determination of light absorption, the extinction coefficient should be greater than $10^3$ mol$^{-1}$cm$^{-1}$, preferably greater than $10^4$ for absorption above the indicated wavelengths.

As indicated previously, one can greatly enhance the detectable signal by having a plurality of mip-enzyme-conjugates bound to the surface for each complementary pair of mips which bind at the surface in relation to the amount of analyte. Thus, for example, by having a receptor such as an antibody from one host and anti-receptor conjugated to an enzyme from a second host, the binding of the receptor to the surface will result in a plurality of anti(receptor)-enzyme-conjugates binding to such receptor. This would have the effect of the enzyme of the conjugate being able to capture a major portion of the product resulting from the enzyme bound to the surface, minimizing the amount of detectable signal producing product produced in the bulk medium.

Another way to reduce background is to have a scavenger in the bulk medium. For example, if the product of the first enzyme is hydrogen peroxide, one could employ catalase or some other reactant in the bulk medium which would destroy the hydrogen peroxide. By having the scavenger in the bulk medium, while there will be some reduction in the overall turnover rates of the two enzymes, one would expect a substantial increase in the ratio of the production of signal producing product related to the amount of analyte as compared to the background signal.

With each enzyme system, different approaches to scavengers may be employed. Desirably, the effect of mip-enzyme-conjugate binding to the surface should provide at least a two, more usually a ten fold and more preferably a 100 fold rate difference than if the mip-enzyme-conjugate was in the bulk solution.

Solid Surface

A wide variety of solid surfaces may be employed, which can include organic or inorganic materials, natural or synthetic, or combinations thereof. Of particular interest are synthetic polymers, particularly addition polymers, such as polystyrene, polyethylene, polypropylene, and the like, usually hydrocarbon polymers.

The solid surface must be capable of binding the mip and the enzyme, either covalently or non-covalently, or made so by functionalization or coating with an appropriate material. A wide variety of functional groups have been employed for modifying unreactive solid surfaces for covalently binding proteins to a surface. The functionalities can include active halide, epoxides, non-oxo-carbonyl compounds, mercaptans, and the like. The particular mode of conjugation of the mip and the enzyme to the surface is not critical to this invention, so long as each retains its properties necessary for the assay.

Alternatively, one can coat the solid surface with a poly(amino acid) e.g. polylysine, and allow the poly(amino acid) to act as an intermediate binding agent between the solid surface and a polypeptide ligand or receptor and the enzyme.

Because the rate of diffusion may undesirably extend the time necessary for obtaining the desired sensitivity, in those situations it will be desirable to greatly enhance the surface area of the solid surface to provide for a shorter average path length for the mip-enzyme-conjugate to encounter the surface. In determining the ratio of the solid surface area to the bulk solution volume, one must consider both the effect of increasing the solid surface area on the amount of enzyme which must then be bound to the surface; and the amount of product this enzyme will produce which will escape into the bulk medium. As the solid surface, vanes having large openings to serve as passages may be employed, particles may be employed, or the like, to provide for the enhanced surface area. Normally, it will be desirable to employ only the container wall.

Ancillary Materials

Various ancillary materials may be employed in the subject assays. Particularly, enzyme substrates, cofactors and inhibitors may be employed as part of the signal producing system. In addition, other materials may include buffers, stabilizers, surfactants, particularly non-ionic surfactants, or the like.

Kits

As a matter of convenience, the reagents can be provided as kits, where the reagents are in predetermined ratios, so as to substantially optimize the sensitivity of the assay in the range of interest. Normally, the reagents will be provided as powders, particularly lyophilized, where the fewest number of individual formulations will be employed as required by the nature of the reagents and the protocol, to minimize the number of separate measurements and additions by the user. In addition, containers, particularly microtiter plates, will be provided, where the mip and enzyme will be bound to the container wall. Included with the mip-enzyme-conjugate, where the enzyme of the conjugate is the second enzyme in the series, may be the substrates and cofactors necessary for the two enzymes. Also included may be various ancillary reagents, as described above.

EXPERIMENTAL

The following examples are offered by way of illustration and not by way of limitation.

(All percents and parts not otherwise indicated are by weight, except for mixtures of liquids which are by volume. All temperatures not otherwise indicated are centigrade.)

The wells of a microtiter plate (Linbro plate, Flow Laboratories) were coated with 200 $\mu$l of polylysine solution (1 mg/ml) for 1–2 hrs. Any unbound polylysine was removed by washing two times with 0.1M sodium acid phosphate, 0.2M NaCl, pH 7.0. The wells were then coated with 50 $\mu$l of a mixture of glucose oxidase (1 mg/ml) and human IgG(10 $\mu$g/ml) for 16 hours at room temperature. Any unbound proteins were removed by washing two times with 0.1M sodium acid phosphate buffer containing 0.2M NaCl, bovine serum albumin (1 mg/ml) and Tween 20(0.02%). The plate was incubated with this washing buffer (200 $\mu$l/well). After two hours, the plate wells were emptied and shaken dry.

For a channeled reaction, 20 $\mu$l of the washing buffer were added to the wells; for an unchanneled reaction, 20 $\mu$l of human IgG(1 mg/ml) were added. By channeled is intended that the product result from two enzymes (GO and HRP) bound to the microtiter plate, while unchanneled intends only one enzyme (GO) is bound to the microtiter plates and the other enzyme (HRP) is free in solution. For the channeling immunoassay, 20 $\mu$l of human IgG at serial dilutions were added. Diluted goat anti-human IgG-horseradish peroxidase-conjugate at about 30 ng active HRP in 30 $\mu$l (Tago, Burlingame, CA) was then added to each well. The plate was incubated for three hours with agitation. To the solution was then added 0.15 ml of substrate (12.5 mM 2,2'-azino-di-(3-ethylbenzothiazoline-6-sulfonic acid [ABTS] and 120 mM glucose) containing 100 $\mu$g of catalase, which is about 600 fold mole excess to horseradish peroxidase. The final volume was 0.2 ml. The absorbance at 414 nm was read on the microtiter plate reader (Flow Laboratories) after 3 h.

The following table indicates the results, these values were averages of two samples.

| HIgG (ng/well) | $A_{414}$ (avg) |
|---|---|
| 0 | 0.457 |
| 0.1 | 0.351 |
| 1 | 0.374 |
| 10 | 0.168 |
| 100 | 0.08 |
| 1,000 | 0.07 |
| 10,000 | 0.02 |

In order to demonstrate the use of non-porous beads, the following experiments were carried out. Polystyrene beads of a size of from about 0.94 $\mu$m(Convaspheres, Covalent Technology Co.) were combined with glucose oxidase and human IgG under conditions where 3-4 ng of active glucose oxidase and 200-400 ng hIgG were bound to the beads in 10 μl of a 0.5% dispersion of the beads. For a channeling reaction, 10 μl of buffer was added, while 10 μl of HIgG(20 μg) was added for an unchanneled reaction. To the mix was then added 30 μl of the conjugate (1:100 dilution, containing about 15 ng active HRP) and the assay medium incubated for about 2.5 hours. In the channeled reaction, the beads agglutinate and precipitate at the bottom of the well, so that the solution becomes clear. In the unchanneled reaction, the solution remains cloudy. To the mixture is then added the substrate solution described above with sufficient catalase to provide about 35 μg/well, a 400:1 mole ratio of catalase to HRP.

The following table indicates the results.

| Time (min) | $A^c414*$ / $A^u414$ |
|---|---|
| 29' | 7.5 |
| 100' | 10.4 |
| 120' | 9.5 |
| 166' | 6.7 |

*absorbance at 414 nm for channeled reaction $^c$ divided by unchanneled $^u$ reaction.

The above results demonstrate that the best ratio of channeled versus unchanneled signal is obtained at about 100 min.

The above data demonstrate that the subject invention provides a simple and rapid way for carrying out assays on a solid surface. Surprisingly, one can accurately differentiate between a channeled reaction, where the two enzymes are on a surface and an unchanneled reaction where one enzyme is on a surface and the other enzyme is dispersed in the solution. The sensitivity is enhanced by the presence of a scavenger in the bulk solution, which destroys the product of the enzyme on the surface, where the product of the enzyme on the surface serves as the substrate for the enzyme of the mip-enzyme-conjugate. The mip-enzyme-conjugate is partitioned between the surface and the bulk solution in relation to the amount of analyte present. The assay is particularly useful in allowing for a method which does not require a physical separation step, nor washing of the walls after the addition of the sample. Nor does the method require the removal of mip-enzyme-conjugate from the bulk solution to allow for the determination of the amount of sample in the assay medium.

Although the foregoing invention has been described in some detail by way of illustration and example for purposes of clarity of understanding, it will be obvious that certain changes and modifications may be practiced within the scope of the appended claims.

What is claimed is:

1. An assay method for determining the presence in a sample of an analyte which is a member of a specific binding pair (msbp) consisting of ligand and its homologous receptor;
   said method employing:
   (a) a continuous aqueous medium;
   (b) a solid non-porous surface which is in contact with said medium and to which is conjugated a msbp and a first enzyme;
   (c) a signal producing system capable of producing a measurable signal, the level of said signal being affected by the concentration of said analyte in said medium, said signal producing system including at least a second enzyme and a substrate for one of said first and second enzymes;
   (d) said second enzyme being conjugated to a msbp to provide a msbp-enzyme-conjugate, wherein the amount of msbp-enzyme-conjugate bound to solid surface is related to the amount of analyte in said aqueous medium;
   wherein the two enzymes are related by the product of one being the substrate of the other;
   said method comprising:
   combining with said solid surface to which said msbp and said first enzyme are conjugated an aqueous medium comprising, (a) said sample; (b) said msbp-enzyme-conjugate; (c) the homologous member of said specific binding pair, when the analyte, msbp-enzyme-conjugate and msbp bound to the surface are the same msbp, and
   (e) substrate for at least one of said enzymes and any remaining members of said signal producing system,
   with the provision that when the analyte is a first receptor, said member of said pair conjugated to said solid surface can be the homologous ligand or receptor for said first receptor and said member of said enzyme conjugate can be receptor for said first receptor or the homologous ligand respectively; and
   determining the level of said signal in said aqueous assay medium as compared to an assay medium having a known amount of analyte.

2. A method according to claim 1, wherein said solid surface is a container wall.

3. A method according to claim 1, wherein said solid surface is a non-porous particle.

4. A method according to claim 1, wherein the pH for the medium is in the range of about 5 to 10.

5. A method according to claim 1, wherein one of the enzymes is a hydrolase.

6. A method according to claim 1 wherein one of said enzymes is an oxidoreductase.

7. A method according to claim 6, wherein said oxidoreductase is an oxidase.

8. A kit for use in a method according to claim 1, comprising in combination a plate having a plurality of wells, wherein bound to the walls of said wells are a first enzyme and a msbp, a msbp-enzyme-conjugate having a second enzyme, wherein said two enzymes are related by the product of one of said enzymes being the substrate of the other of said enzymes, and at least one substrate for said enzymes, wherein said msbp-enzyme-conjugate becomes bound to said walls through the intermediacy of the homologous msbp, so as to bring the two enzymes into close proximity on said walls as a result of the amount of homologous msbp which is combined with the kit components in said method.

9. A kit according to claim 8, wherein the two enzymes are oxidoreductases.

10. A kit according to claim 9, wherein one of said oxidoreductases is glucose oxidase and the other of said oxidoreductases is horseradish peroxidase.

11. A kit according to claim 10, wherein said substrate includes a dye oxidized by a reaction catalyzed by horseradish peroxidase.

12. An assay method for determining the presence in a sample of a member of a specific binding pair (msbp) consisting of ligand and its homologous receptor, wherein said method employs:

(1) a medium comprised of an aqueous buffered continuous phase at a pH in the range of about 6.5 to 9.5 and a solid non-porous phase as a support to which is conjugated one of the members of said specific binding pair and a first enzyme to provide a conjugated support, and (2) a signal producing system capable of producing a measurable signal and having a second enzyme conjugated to a msbp to provide a msbp-enzyme-conjugate, wherein said first and second enzymes with appropriate substrates and cofactors define said signal producing system and said first and second enzymes are related by the product of one being the substrate of the other, wherein said measurable signal varies in relation to the partitioning of said msbp-enzyme-conjugate between said support and said aqueous medium, said partitioning being related to the amount of analyte in said medium, said method comprising:

combining said support to which said msbp and said first enzyme are conjugated and said aqueous medium comprising (a) said sample; (b) said msbp-enzyme-conjugate; (c) the homologous member of said specific binding pair, when said analyte, support and msbp-enzyme-conjugate have the same msbp, and (d) substrate and any additional members of said signal producing system, whereby said msbp-enzyme-conjugate will be partitioned between said aqueous medium and said support in an amount dependent upon the amount of analyte in said sample; and determining the level of said signal in said assay medium as compared to a assay medium having a known amount of analyte.

13. A method according to claim 12, wherein both enzymes are oxidoreductases.

14. A method according to claim 13, wherein one of said enzymes produces hydrogen peroxide.

15. A method according to claim 14, where included in said aqueous medium is an enzyme hydrogen peroxide scavenger.

16. A method according to claim 14, wherein one of said enzymes is glucose oxidase and the other of said enzymes is horseradish peroxidase.

* * * * *